(12) United States Patent
Dharmarajan et al.

(10) Patent No.: US 7,902,093 B2
(45) Date of Patent: Mar. 8, 2011

(54) ELASTOMERIC NONWOVENS

(75) Inventors: Narayanaswami Raja Dharmarajan, Houston, TX (US); Smita Kacker, Houston, TX (US)

(73) Assignee: Exxonmobil Chemical Patents Inc., Houston, TX (US)

( * ) Notice: Subject to any disclaimer, the term of this patent is extended or adjusted under 35 U.S.C. 154(b) by 154 days.

(21) Appl. No.: 11/698,630

(22) Filed: Jan. 26, 2007

(65) Prior Publication Data

US 2008/0182468 A1 Jul. 31, 2008

(51) Int. Cl.
*D04H 5/04* (2006.01)
(52) U.S. Cl. ............... 442/328; 442/329; 442/381
(58) Field of Classification Search ............ 442/327, 442/328, 329, 381
See application file for complete search history.

(56) References Cited

U.S. PATENT DOCUMENTS

| | | | | |
|---|---|---|---|---|
| 4,472,485 A | | 9/1984 | Tabuse et al. ............... 428/516 |
| 5,114,646 A | * | 5/1992 | Nohr et al. ................. 264/103 |
| 5,226,992 A | * | 7/1993 | Morman ................... 156/62.4 |
| 5,393,599 A | | 2/1995 | Quantrille et al. .......... 428/284 |
| 5,418,045 A | | 5/1995 | Pike et al. .................. 428/198 |
| 5,733,617 A | | 3/1998 | Bauduel .................... 428/36.8 |
| 5,840,412 A | | 11/1998 | Wood et al. ................ 428/284 |
| 5,914,184 A | | 6/1999 | Morman ................... 428/315.9 |
| 5,921,973 A | | 7/1999 | Newkirk et al. ............ 604/365 |
| 6,015,764 A | | 1/2000 | McCormack et al. ....... 442/370 |
| 6,103,647 A | * | 8/2000 | Shultz et al. ............... 442/346 |
| 6,114,596 A | * | 9/2000 | Nayak et al. ............... 604/370 |
| 6,148,817 A | | 11/2000 | Bryant et al. ............ 128/207.11 |
| 6,342,565 B1 | * | 1/2002 | Cheng et al. ................ 525/191 |
| 6,516,472 B2 | | 2/2003 | Gessner et al. ................. 2/111 |
| 6,531,207 B1 | | 3/2003 | Eaton et al. ................. 428/198 |
| 2004/0087235 A1 | | 5/2004 | Morman et al. ............. 442/394 |
| 2004/0186214 A1 | * | 9/2004 | Li et al. ...................... 524/474 |
| 2005/0096623 A1 | | 5/2005 | Nhan et al. ............. 604/385.22 |
| 2005/0106978 A1 | * | 5/2005 | Cheng et al. ................ 442/327 |

FOREIGN PATENT DOCUMENTS

| | | |
|---|---|---|
| EP | 0 832 629 A2 | 4/1998 |
| EP | 1 069 223 A1 | 1/2001 |
| EP | 1 138 472 A1 | 10/2001 |
| WO | 2005/019515 | 3/2005 |
| WO | 2006/044083 | 4/2006 |

OTHER PUBLICATIONS

Inventors: Dharmarajan et al., entitled "Elastomeric Laminates for Consumer Products", filed Jan. 26, 2007.
Abstract—JP 09078431, Mar. 25, 2007.
M. G. Kamath, et al., *Finishing of Nonwoven Bonded Fabrics*, The University of Tennessee Knoxville, Materials Science & Engineering 554, Nonwovens Science and Technology II, Spring 2004, pp. 1-11.

* cited by examiner

*Primary Examiner* — D. Lawrence Tarazano
*Assistant Examiner* — Peter Y Choi

(57) ABSTRACT

A nonwoven fabric and disposable articles comprising the same are provided. The nonwoven fabric can include one or more facing layers thermally bonded to one or more inner layers. The facing layers are inelastic or partially elastic nonwoven webs comprising one or more propylene-based polymers. The facing layer has a permanent set above 30%. The inner layers are elastic nonwoven webs comprising one or more propylene-based polymers and one or more slip agents. The inner layer has a permanent set below 28%, and the one or more propylene-based polymers have (i) 60 wt % or more units derived from propylene, (ii) isotactically arranged propylene derived sequences, and (iii) a heat of fusion less than 45 J/g.

26 Claims, No Drawings

ELASTOMERIC NONWOVENS

BACKGROUND OF THE INVENTION

1. Field of the Invention

Embodiments of the present invention generally relate to non-wovens. More particularly, embodiments of the present invention relate to non-woven fabrics containing propylene-based polymers.

2. Description of the Related Art

Elastic nonwoven materials are used in personal care products including diapers, adult incontinence wear, and other personal hygiene products. Such elastic nonwoven materials are typically constructed of elastomer and/or elastomer-like polymers that provide stretchability and that are tailored for processing in conventional spunmelt equipment.

Nonwoven materials with good stretchability and elasticity are particularly desirable for such personal care products. For clothing, stretchability and elasticity are performance attributes that allow the nonwoven material to provide a closely conforming fit to the body of the wearer. However, elastic materials inherently have a "rubbery" feel that is unacceptable from a consumer's perspective in applications involving contact with human skin. Accordingly, elastic materials have been modified to have a more pleasant feel; yet such modification of the spunmelt polymers has a tendency to compromise the physical and elastic properties of the resulting nonwoven material.

There is a need, therefore, for improving the feel of non-woven fabrics containing elastomer and/or elastomer-like polymers without compromising the physical and elastic properties of the material.

SUMMARY OF THE INVENTION

A nonwoven fabric and disposable article comprising the same are provided. In at least one specific embodiment, the nonwoven fabric comprises one or more facing layers thermally bonded to one or more inner layers, wherein: the facing layers are inelastic or partially elastic nonwoven webs comprising one or more propylene-based polymers, the facing layer having a permanent set above 30%; the inner layers are elastic nonwoven webs comprising one or more propylene-based polymers and one or more slip agents, the inner layer having a permanent set below 28%; and the one or more propylene-based polymers have (i) 60 wt % or more units derived from propylene, (ii) isotactically arranged propylene derived sequences, and (iii) a heat of fusion less than 45 J/g.

In another specific embodiment, the nonwoven fabric includes an inelastic nonwoven facing layer or layers comprising at least one polyolefin polymer, the inelastic layer having a permanent set above 30%; and an elastic nonwoven layer or layers adjacent to the inelastic facing layer comprising a propylene-based polymer having 60 wt % or more units derived from propylene and isotactically arranged propylene derived sequences, the elastic layer having a permanent set below 28%.

In yet another specific embodiment, the nonwoven fabric includes one or more facing layers thermally bonded to one or more inner layers, wherein the facing layers are inelastic or partially elastic nonwoven webs comprising a blend of one or more propylene-based polymers and polypropylene, and wherein the inner layers are elastic nonwoven webs comprising one or more propylene-based polymers and one or more slip agents, and wherein the facing layers and inner layers have a difference in permanent set of at least 5%.

DETAILED DESCRIPTION

A nonwoven fabric having good stretchability, elasticity and feel is provided. In one or more embodiments, the non-woven fabric includes one or more inelastic or semi-elastic facing layers that are thermally bonded to one or more elastic inner layers. Preferably, each of the one or more facing layers and the inner layers are nonwoven. The resulting nonwoven fabric or elastic laminate can have any number of facing layers ("A") and any number of inner layers ("B").

The terms "nonwoven," "nonwoven fabric," and "non-woven web" as used herein, are used interchangeably and refer to a web or fabric that has a structure of individual fibers or filaments that are randomly interlaid, but not in an identifiable repeating pattern.

The terms "elastic" and "semi-elastic" refer to any material having a tension set of 80% or less, or 60% or less, or 50% or less, or 25% or less, at 100% elongation at a temperature between the glass transition temperature and the crystalline melting point. Elastic polymer materials and compositions are also referred to in the art as "elastomers" and "elastomeric."

Facing Layer

In one or more embodiments, at least one facing layer is or includes polypropylene. In one or more embodiments, at least one facing layer is or includes a blend of one or more propylene-based polymers and polypropylene. In one or more embodiments, at least one facing layer is or includes a blend of one or more propylene-based polymers, polypropylene, and one or more thermoplastic resins.

Inner Layer

In one or more embodiments, the one or more inner layers is or includes one or more propylene-based polymers. In one or more embodiments, the one or more inner layers is or includes a blend of one or more propylene-based polymers and one or more slip agents. In one or more embodiments, the one or more inner layers is or includes a blend of one or more propylene-based polymers, one or more slip agents, and one or more hydrocarbon resins. In one or more embodiments above or elsewhere herein, any one or more of the inner layers can further include one or more thermoplastic resins.

As mentioned above, the one or more facing layers are thermally bonded to the one or more inner layers. The layers can be thermally bonded using a calendering process or any other process known in the art. It is believed that the "rubbery feel" that is intrinsic to an unmodified elastic nonwoven is eliminated by way of the inner layer(s) containing one or more slip agents and/or one or more hydrocarbon resins. As such, the modified elastic nonwoven has an appealing touch to the wearer.

As used herein, the term "thermal bonding" refers to the heating of fibers to effect the melting (or softening) and fusing of fibers such that a nonwoven fabric is produced. Thermal bonding includes calendar bonding and through-air bonding, as well as other methods known in the art.

Not wishing to be bound by theory, it is believed that the nonwoven inner layer modified with the slip agent(s) has an acceptable feel; however, the presence of the slip, which has a tendency to migrate to the surface, causes interference with adhesion of other ancillary components to the nonwoven. For example, the migration of a slip in a diaper can cause the diaper tabs to lose adhesion and fail. Therefore, having a facing layer that is devoid of slip provides an anchor for the adhesion, while the opposite side of the fabric is bestowed with an acceptable feel from the presence of the slip. Such a construction serves the dual purpose of an adhesion enabling layer (the "one or more facing layers") that has a dry touch, and a "silky, satin" type feel when in contact with skin.

Propylene-Based Polymer

The propylene-based polymer can be propylene-α-olefin copolymers, propylene-α-olefin-diene terpolymers, or propylene-diene copolymers. For simplicity and ease of description, however, the term "propylene-based polymer" as used herein refers to propylene-α-olefin copolymers, propylene-α-olefin-diene terpolymers, and propylene-diene copolymers.

The propylene-based polymer can be prepared by polymerizing propylene with one or more comonomers. In at least one embodiment, the propylene-based polymer can be prepared by polymerizing propylene with one or more $C_2$ and/or $C_4$-$C_8$ α-olefin. In at least one other specific embodiment, the propylene-based polymer can be prepared by polymerizing propylene with one or more dienes. In at least one other specific embodiment, the propylene-based polymer can be prepared by polymerizing propylene with ethylene and/or at least one $C_4$-$C_{20}$ α-olefin, or a combination of ethylene and/or at least one $C_4$-$C_{20}$ α-olefin and one or more dienes. The one or more dienes can be conjugated or non-conjugated. Preferably, the one or more dienes are non-conjugated.

The comonomers can be linear or branched. Preferred linear comonomers include ethylene or $C_4$ to $C_8$ α-olefins, more preferably ethylene, 1-butene, 1-hexene, and 1-octene, even more preferably ethylene or 1-butene. Preferred branched comonomers include 4-methyl-1-pentene, 3-methyl-1-pentene, and 3,5,5-trimethyl-1-hexene. In one or more embodiments, the comonomer can include styrene.

Illustrative dienes can include but are not limited to 5-ethylidene-2-norbornene (ENB); 1,4-hexadiene; 5-methylene-2-norbornene (MNB); 1,6-octadiene; 5-methyl-1,4-hexadiene; 3,7-dimethyl-1,6-octadiene; 1,3-cyclopentadiene; 1,4-cyclohexadiene; vinyl norbornene (VNB); dicyclopendadiene (DCPD), and combinations thereof. Preferably, the diene is ENB.

Preferred methods and catalysts for producing the propylene-based polymers are found in publications US 2004/0236042 and WO 05/049672 and in U.S. Pat. No. 6,881,800, which are all incorporated by reference herein. Pyridine amine complexes, such as those described in WO03/040201 are also useful to produce the propylene-based polymers useful herein. The catalyst can involve a fluxional complex, which undergoes periodic intra-molecular re-arrangement so as to provide the desired interruption of stereoregularity as in U.S. Pat. No. 6,559,262. The catalyst can be a stereorigid complex with mixed influence on propylene insertion, see Rieger EP1070087. The catalyst described in EP1614699 could also be used for the production of backbones suitable for the invention.

The propylene-based polymer can have an average propylene content on a weight percent basis of from about 60 wt % to about 99.7 wt %, more preferably from about 60 wt % to about 99.5 wt %, more preferably from about 60 wt % to about 97 wt %, more preferably from about 60 wt % to about 95 wt % based on the weight of the polymer. In one embodiment, the balance comprises a $C_2$ and/or $C_4$-$C_8$ α-olefin. In another embodiment, the balance comprises diene. In another embodiment, the balance comprises one or more dienes and one or more of the α-olefins described previously. Other preferred ranges are from about 80 wt % to about 95 wt % propylene, more preferably from about 83 wt % to about 95 wt % propylene, more preferably from about 84 wt % to about 95 wt % propylene, and more preferably from about 84 wt % to about 94 wt % propylene based on the weight of the polymer. The balance of the propylene-based polymer comprises a diene and optionally, one or more alpha-olefins. In one or more embodiments above or elsewhere herein, the alpha-olefin is butene, hexene or octene. In other embodiments, two alpha-olefins are present, preferably ethylene and one of butene, hexene or octene.

Preferably, the propylene-based polymer comprises about 0.3 wt % to about 24 wt %, of a non-conjugated diene based on the weight of the polymer, more preferably from about 0.5 wt % to about 12 wt %, more preferably about 0.6 wt % to about 8 wt %, and more preferably about 0.7 wt % to about 5 wt %. In other embodiments, the diene content ranges from about 0.3 wt % to about 10 wt %, more preferably from about 0.3 to about 5 wt %, more preferably from about 0.3 wt % to about 4 wt %, preferably from about 0.3 wt % to about 3.5 wt %, preferably from about 0.3 wt % to about 3.0 wt %, and preferably from about 0.3 wt % to about 2.5 wt % based on the weight of the polymer. In one or more embodiments above or elsewhere herein, the propylene-based polymer comprises ENB in an amount of from about 0.5 to about 4 wt %, more preferably from about 0.5 to about 2.5 wt %, and more preferably from about 0.5 to about 2.0 wt %.

In other embodiments, the propylene-based polymer comprises propylene and diene in one or more of the ranges described above with the balance comprising one or more $C_2$ and/or $C_4$-$C_{20}$ olefins. In general, this will amount to the propylene-based polymer preferably comprising from about 5 to about 40 wt % of one or more $C_2$ and/or $C_4$-$C_{20}$ olefins based the weight of the polymer. When $C_2$ and/or a $C_4$-$C_{20}$ olefins are present the combined amounts of these olefins in the polymer is preferably at least about 5 wt % and falling within the ranges described herein. Other preferred ranges for the one or more α-olefins include from about 5 wt % to about 35 wt %, more preferably from about 5 wt % to about 30 wt %, more preferably from about 5 wt % to about 25 wt %, more preferably from about 5 wt % to about 20 wt %, more preferably from about 5 to about 17 wt % and more preferably from about 5 wt % to about 16 wt %.

The propylene-based polymer can have a weight average molecular weight (Mw) of about 5,000,000 or less, a number average molecular weight (Mn) of about 3,000,000 or less, a z-average molecular weight (Mz) of about 10,000,000 or less, and a g' index of 0.95 or greater measured at the weight average molecular weight (Mw) of the polymer using isotactic polypropylene as the baseline, all of which can be determined by size exclusion chromatography, e.g., 3D SEC, also referred to as GPC-3D as described herein.

In one or more embodiments above or elsewhere herein, the propylene-based polymer can have a Mw of about 5,000 to about 5,000,000 g/mole, more preferably a Mw of about 10,000 to about 1,000,000, more preferably a Mw of about 20,000 to about 500,000, more preferably a Mw of about 50,000 to about 400,000, wherein Mw is determined as described herein.

In one or more embodiments above or elsewhere herein, the propylene-based polymer can have a Mn of about 2,500 to about 2,500,000 g/mole, more preferably a Mn of about 5,000 to about 500,000, more preferably a Mn of about 10,000 to about 250,000, more preferably a Mn of about 25,000 to about 200,000, wherein Mn is determined as described herein.

In one or more embodiments above or elsewhere herein, the propylene-based polymer can have a Mz of about 10,000 to about 7,000,000 g/mole, more preferably a Mz of about 50,000 to about 1,000,000, more preferably a Mz of about 80,000 to about 700,000, more preferably a Mz of about 100,000 to about 500,000, wherein Mz is determined as described herein.

The molecular weight distribution index (MWD=(Mw/Mn)), sometimes referred to as a "polydispersity index" (PDI), of the propylene-based polymer can be about 1.5 to 40. In an embodiment the MWD can have an upper limit of 40, or 20, or 10, or 5, or 4.5, and a lower limit of 1.5, or 1.8, or 2.0. In one or more embodiments above or elsewhere herein, the MWD of the propylene-based polymer is about 1.8 to 5 and most preferably about 1.8 to 3. Techniques for determining the molecular weight (Mn and Mw) and molecular weight distribution (MWD) can be found in U.S. Pat. No. 4,540,753 (Cozewith, Ju and Verstrate) (which is incorporated by reference herein for purposes of U.S. practices) and references cited therein, in Macromolecules, 1988, volume 21, p 3360 (Verstrate et al.), which is herein incorporated by reference for purposes of U.S. practice, and references cited therein, and in accordance with the procedures disclosed in U.S. Pat. No. 6,525,157, column 5, lines 1-44, which patent is hereby incorporated by reference in its entirety.

In one or more embodiments above or elsewhere herein, the propylene-based polymer can have a g' index value of 0.95 or greater, preferably at least 0.98, with at least 0.99 being more preferred, wherein g' is measured at the Mw of the polymer using the intrinsic viscosity of isotactic polypropylene as the baseline. For use herein, the g' index is defined as:

$$g' = \frac{\eta_b}{\eta_l}$$

where $\eta_b$ is the intrinsic viscosity of the propylene-based polymer and $\eta_l$ is the intrinsic viscosity of a linear polymer of the same viscosity-averaged molecular weight ($M_v$) as the propylene-based polymer. $\eta_l = KM_v^\alpha$, K and $\alpha$ are measured values for linear polymers and should be obtained on the same instrument as the one used for the g' index measurement.

In one or more embodiments above or elsewhere herein, the propylene-based polymer can have a density of about 0.85 g/cm³ to about 0.92 g/cm³, more preferably, about 0.87 g/cm³ to 0.90 g/cm³, more preferably about 0.88 g/cm³ to about 0.89 g/cm³ at room temperature as measured per ASTM D-1505.

In one or more embodiments above or elsewhere herein, the propylene-based polymer can have a melt flow rate (MFR, 2.16 kg weight@ 230° C.), equal to or greater than 0.2 g/10 min as measured according to ASTM D-1238(A) as modified (described below). Preferably, the MFR (2.16 kg (230° C.) is from about 0.5 g/10 min to about 200 g/10 min and more preferably from about 1 g/10 min to about 100 g/10 min. In an embodiment, the propylene-based polymer has an MFR of from about 0.5 g/10 min to about 200 g/10 min, especially from about 2 g/10 min to about 30 g/10 min, more preferably from about 5 g/10 min to about 30 g/10 min, more preferably from about 10 g/10 min to about 30 g/10 min or more especially from about 10 g/10 min to about 25 g/10 min.

The propylene-based polymer can have a Mooney viscosity, ML (1+4)@125° C., as determined according to ASTM D1646, of less than 100, more preferably less than 75, even more preferably less than 60, and most preferably less than 30.

In one or more embodiments above or elsewhere herein, the propylene-based polymer can have a heat of fusion (Hf) determined according to the DSC procedure described later which is greater than or equal to about 0.5 Joules per gram (J/g), and is ≦about 80 J/g, preferably ≦about 75 J/g, preferably ≦about 70 J/g, more preferably ≦about 60 J/g, more preferably ≦about 50 J/g, more preferably ≦about 45 J/g, more preferably ≦about 35 J/g. Also preferably, the propylene-based polymer has a heat of fusion that is greater than or equal to about 1 J/g, preferably greater than or equal to about 5 J/g. In another embodiment, the propylene-based polymer can have a heat of fusion (Hf), which is from about 0.5 J/g to about 75 J/g, preferably from about 1 J/g to about 75 J/g, more preferably from about 0.5 J/g to about 35 J/g. Preferred propylene-based polymers and compositions can be characterized in terms of both their melting points (TM) and heats of fusion, which properties can be influenced by the presence of comonomers or steric irregularities that hinder the formation of crystallites by the polymer chains. In one or more embodiments, the heat of fusion ranges from a lower limit of 1.0 J/g, or 1.5 J/g, or 3.0 J/g, or 4.0 J/g, or 6.0 J/g, or 7.0 J/g, to an upper limit of 30 J/g, or 35 J/g, or 40 J/g, or 45 J/g, or 50 J/g, or 60 J/g or 70 J/g, or 75 J/g, or 80 J/g.

The crystallinity of the propylene-based polymer can also be expressed in terms of percentage of crystallinity (i.e. % crystallinity). In one or more embodiments above or elsewhere herein, the propylene-based polymer has a % crystallinity of from 0.5% to 40%, preferably 1% to 30%, more preferably 5% to 25% wherein % crystallinity is determined according to the DSC procedure described below. In another embodiment, the propylene-based polymer preferably has a crystallinity of less than 40%, preferably about 0.25% to about 25%, more preferably from about 0.5% to about 22%, and most preferably from about 0.5% to about 20%. As disclosed above, the thermal energy for the highest order of polypropylene is estimated at 189 J/g (i.e., 100% crystallinity is equal to 189 J/g.).

In addition to this level of crystallinity, the propylene-based polymer preferably has a single broad melting transition. However, the propylene-based polymer can show secondary melting peaks adjacent to the principal peak, but for purposes herein, such secondary melting peaks are considered together as a single melting point, with the highest of these peaks (relative to a baseline as described herein) being considered the melting point of the propylene-based polymer.

The propylene-based polymer preferably has a melting point (measured by DSC) of equal to or less than 105° C., preferably less than 100° C., preferably less than 90° C., preferably less than 80° C., more preferably less than or equal to 75° C., preferably from about 25° C. to about 80° C., preferably about 25° C. to about 75° C., more preferably about 30° C. to about 65° C.

The Differential Scanning Calorimetry (DSC) procedure can be used to determine heat of fusion and melting temperature of the propylene-based polymer. The method is as follows: About 6 to 10 mg of a sheet of the polymer pressed at approximately 200° C. to 230° C. and allowed to cool by hanging in air under ambient conditions, is removed with a punch die and annealed at room temperature for 48 hours. At the end of this period, the sample is placed in a Differential Scanning Calorimeter (Perkin Elmer Pyris 1 Thermal Analysis System) and cooled to about −50° C. to −70° C. The sample is heated at about 20° C./min to attain a final temperature of about 180° C. to 200° C. The term "melting point," as used herein, is the highest peak among principal and secondary melting peaks as determined by DSC, discussed above. The thermal output is recorded as the area under the melting peak of the sample, which is typically at a maximum peak at about 30° C. to about 175° C. and occurs between the temperatures of about 0° C. and about 200° C. The thermal output is measured in Joules as a measure of the heat of fusion. The melting point is recorded as the temperature of the greatest heat absorption relative to a baseline measurement within the range of melting of the sample.

The propylene-based polymer can have a triad tacticity of three propylene units, as measured by $^{13}$C NMR, of 75% or greater, 80% or greater, 82% or greater, 85% or greater, or 90% or greater. Preferred ranges include from about 50 to about 99%, more preferably from about 60 to about 99%, more preferably from about 75 to about 99% and more preferably from about 80 to about 99%; and in other embodiments from about 60 to about 97%. Triad tacticity is determined by the methods described in U.S. Patent Application Publication 20040236042.

In one or more embodiments above or elsewhere herein, the propylene-based polymer can be a blend of discrete random propylene-based polymers. Such blends can include ethylene-based polymers and propylene-based polymers, or at least one of each such ethylene-based polymers and propylene-based polymers. The number of propylene-based polymers can be three or less, more preferably two or less.

In one or more embodiments above or elsewhere herein, the propylene-based polymer can include a blend of two propylene-based polymers differing in the olefin content, the diene content, or both.

In one or more embodiments above or elsewhere herein, the propylene-based polymer can include a propylene based elastomeric polymer produced by random polymerization processes leading to polymers having randomly distributed irregularities in stereoregular propylene propagation. This is in contrast to block copolymers in which constituent parts of the same polymer chains are separately and sequentially polymerized.

In another embodiment, the propylene-based polymers can include copolymers prepared according the procedures in WO 02/36651. Likewise, the propylene-based polymer can include polymers consistent with those described in WO 03/040201, WO 03/040202, WO 03/040095, WO 03/040201, WO 03/040233, and/or WO 03/040442. Additionally, the propylene-based polymer can include polymers consistent with those described in EP 1 233 191, and U.S. Pat. No. 6,525,157, along with suitable propylene homo- and copolymers described in U.S. Pat. No. 6,770,713 and U.S. Patent Application Publication 2005/215964, all of which are incorporated by reference. The propylene-based polymer can also include one or more polymers consistent with those described in EP 1 614 699 or EP 1 017 729.

Polypropylene

The term "polypropylene" as used herein broadly means any polymer that is considered a "polypropylene" by persons skilled in the art (as reflected in at least one patent or publication), and includes homo, impact, and random polymers of propylene. Preferably, the polypropylene used in the compositions described herein has a melting point above 110° C., includes at least 90 wt % propylene units, and contains isotactic sequences of those units. The polypropylene can also include atactic sequences or syndiotactic sequences, or both. The polypropylene can either derive exclusively from propylene monomers (i.e., having only propylene units) or derive from mainly propylene (more than 80% propylene) with the remainder derived from olefins, particularly ethylene, and/or $C_4$-$C_{10}$ alpha-olefins. The polypropylene can have a high MFR (e.g., from a low of 10, or 15, or 20 g/10 min to a high of 25 to 30 g/10 min. The polypropylene can also have a lower MFR, e.g., "fractional" polypropylenes which have an MFR less than 1.0. Those with high MFR are preferred for ease of processing or compounding.

In one or more embodiments, the polypropylene is or includes isotactic polypropylene. Preferably, the polypropylene contains one or more crystalline propylene homopolymers or copolymers of propylene having a melting temperature of from 110° C. to 170° C. or higher as measured by DSC. Preferred copolymers of propylene include, but are not limited to, terpolymers of propylene, impact copolymers of propylene, random polypropylene and mixtures thereof. Preferred comonomers have 2 carbon atoms, or from 4 to 12 carbon atoms. Preferably, the comonomer is ethylene. Such polypropylenes and methods for making the same are described in U.S. Pat. No. 6,342,565.

The term "random polypropylene" as used herein broadly means a single phase copolymer of propylene having up to 9 wt %, preferably 2 wt % to 8 wt % of an alpha olefin comonomer. Preferred alpha olefin comonomers have 2 carbon atoms, or from 4 to 12 carbon atoms. Preferably, the alpha olefin comonomer is ethylene.

Thermoplastic Resin

In one or more embodiments, the thermoplastic resin includes an olefinic thermoplastic resin. The "olefinic thermoplastic resin" can be any material that is not a "rubber" and that is a polymer or polymer blend considered by persons skilled in the art as being thermoplastic in nature, e.g., a polymer that softens when exposed to heat and returns to its original condition when cooled to room temperature. The olefinic thermoplastic resin can contain one or more polyolefins, including polyolefin homopolymers and polyolefin copolymers. Except as stated otherwise, the term "copolymer" means a polymer derived from two or more monomers (including terpolymers, tetrapolymers, etc.), and the term "polymer" refers to any carbon-containing compound having repeat units from one or more different monomers.

Illustrative polyolefins can be prepared from mono-olefin monomers including, but are not limited to, monomers having 2 to 8 carbon atoms, such as ethylene, propylene, 1-butene, isobutylene, 1-pentene, 1-hexene, 1-octene, 3-methyl-1-pentene, 4-methyl-1-pentene, 5-methyl-1-hexene, mixtures thereof and copolymers thereof with (meth)acrylates and/or vinyl acetates. Preferably, the olefinic thermoplastic resin is unvulcanized or non cross-linked. In embodiments where a blend includes polypropylene, the thermoplastic resin is not a polypropylene.

Hydrocarbon Resin

The inner layer can include one or more hydrocarbon resins. The one or more hydrocarbon resins can be used to improve processability. The one or more hydrocarbon resin can also be used to modify the touch properties of the elastic nonwoven.

The one or more hydrocarbon resins can be grafted or not grafted. Optionally, the resin can be hydrogenated. Preferably, the one or more hydrocarbon resins are low molecular weight hydrocarbon(s) that are compatible with the core layer. The resin can have a number average molecular weight (Mn) less than about 5000, preferably less than about 2000, most preferably in the range of from about 500 to about 1000. The resin can be natural or synthetic and can have a softening point in the range of from about 60° C. to about 180° C.

Suitable hydrocarbon resins can include, but are not limited to petroleum resins, terpene resins, styrene resins, and cyclopentadiene resins. In one or more embodiments, the hydrocarbon resin is selected from the group consisting of aliphatic hydrocarbon resins, hydrogenated aliphatic hydrocarbon resins, aliphatic/aromatic hydrocarbon resins, hydrogenated aliphatic/aromatic hydrocarbon resins, cycloaliphatic hydrocarbon resins, hydrogenated cycloaliphatic resins, cycloaliphatic/aromatic hydrocarbon resins, hydrogenated cycloaliphatic/aromatic hydrocarbon resins, hydrogenated aromatic hydrocarbon resins, polyterpene resins, terpene-phenol resins, rosins and rosin esters, hydrogenated rosins and rosin esters, and combinations thereof.

Suitable hydrocarbon resins include EMPR 120, 104, 111, 106, 112, 115, EMFR 100 and 100A, ECR-373 and ESCOREZ® 2101, 2203, 2520, 5380, 5600, 5618, 5690 (commercially available from ExxonMobil Chemical Company of Baytown, Tex., USA); ARKON™ M90, M100, M115 and M135 and SUPER ESTER™ rosin esters (commercially available from Arakawa Chemical Company of Japan); SYLVARES™ phenol modified styrene, methyl styrene resins, styrenated terpene resins, ZONATAC™ terpene-aromatic resins, and terpene phenolic resins (commercially available from Arizona Chemical Company of Jacksonville, Fla., USA); SYLVATAC™ and SYLVALITE™ rosin esters (commercially available from Arizona Chemical Company of Jacksonville, Fla., USA); NORSOLENE™ aliphatic aromatic resins (commercially available from Cray Valley of France); DERTOPHENE™ terpene phenolic resins (commercially available from DRT Chemical Company of Landes, France); EASTOTAC™ resins, PICCOTAC™ $C_5/C_9$ resins, REGALITE™ and REGALREZ™ aromatic and REGALITE™ cycloaliphatic/aromatic resins (commercially available from Eastman Chemical Company of Kingsport, Tenn.); WINGTACK™ ET and EXTRA™ (commercially available from Sartomer of Exton, Pa., USA); FORAL™, PENTALYN™, and PERMALYN™ rosins and rosin esters (commercially available from Hercules, now Eastman Chemical Company of Kingsport, Tenn., USA); QUINTONE™ acid modified $C_5$ resins, $C_5/C_9$ resins, and acid modified $C_5/C_9$ resins (commercially available from Nippon Zeon of Japan); LX™ mixed aromatic/cycloaliphatic resins (commercially available from Neville Chemical Company of Pittsburgh, Pa., USA); CLEARON™ hydrogenated terpene aromatic resins (commercially available from Yasuhara of Japan); and PICCOLYTE™ (commercially available from Loos & Dilworth, Inc. of Bristol, Pa., USA). Other suitable hydrocarbon resins may be found in U.S. Pat. No. 5,667,902.

Preferred hydrocarbon resins include saturated alicyclic resins. Such resins, if used, can have a softening point in the range of from about 85° C. to about 140° C., or preferably in the range of about 100° C. to about 140° C., as measured by the ring and ball technique. Examples of suitable, commercially available saturated alicyclic resins are ARKON-P® resins (commercially available from Arakawa Forest Chemical Industries, Ltd., of Japan).

The amount of the one or more hydrocarbon resins, either alone or in combination, in the inner layer is preferably less than about 20 wt %, and more preferably in the range of from about 1 wt % to about 5 wt %, based on the total weight of the core layer.

Slip Agents

Illustrative slip agents include fatty acids, higher aliphatic acid amides, higher aliphatic acid esters, waxes and metal soaps. In one or more embodiments, the slip agents can include one or more amides such as behenamide, ercamide, N-(2-hydroxytehyl) erucamide, lauramide, N,N'-ethylene bis-olamide, oleamide, oleyl palmitamide, stearyl, erucamide, tallow amide, blends thereof, and combinations thereof. In one or more embodiments, the slip agents are added to the blend in amounts ranging from about 0.1 to about 2 weight percent based on the total weight of the blend.

Blending and Additives

In one or more embodiments, the one or more propylene-based polymers, polypropylene, thermoplastic resins, slip agents, and or hydrocarbon resins can be blended by melt-mixing to form a blend. In one or more embodiments, the blend contains no processing oil. In other words, the blend is processed in the absence of processing oil. The blend can be prepared and mixed using extruders with kneaders or mixing elements with one or more mixing tips or flights, extruders with one or more screws, extruders of co or counter rotating type, Banbury mixer, Farrell Continuous mixer, and the Buss Kneader. The type and intensity of mixing, temperature, and residence time required can be achieved by the choice of one of the above machines in combination with the selection of kneading or mixing elements, screw design, and screw speed (<3000 RPM).

In one or more embodiments, the one or more facing layers include at least 60 wt % of a propylene-based polymer. The one or more facing layers can include at least 70 wt % of a propylene-based polymer. The one or more facing layers can include at least 80 wt % of a propylene-based polymer. The one or more facing layers can include at least 90 wt % of a propylene-based polymer. The one or more facing layers can include at least 95 wt % of a propylene-based polymer.

In one or more embodiments, the facing layer blend can include the propylene-based polymer in an amount ranging from a low of about 60, 70, or 75 wt % to a high of about 80, 90, or 95 wt %. In one or more embodiments, the facing layer blend can include polypropylene in an amount ranging from a low of about 5, 10, or 20 wt % to a high of about 25, 30, or 40 wt %. In one or more embodiments, the facing layer blend can include the one or more polyolefinic thermoplastic components in an amount ranging from a low of about 5, 10 or 20 wt % to a high of about 25, 30, or 40 wt %.

In one or more embodiments, the facing layer blend can include about 70 wt % to about 95 wt % of the propylene-based polymer and about 5 wt % to about 30 wt % of polypropylene. In one or more embodiments, the facing layer blend can include about 65 wt % to about 80 wt % of the propylene-based polymer and about 20 wt % to about 35 wt % of polypropylene. When the one or more thermoplastic resins are present, the facing layer blend can include about 60 wt % to about 95 wt % of the propylene-based polymer and about 5 wt % to about 40 wt % of polypropylene.

In one or more embodiments, the one or more inner layers include at least 60 wt % of a propylene-based polymer. The one or more inner layers can include at least 70 wt % of a propylene-based polymer. The one or more inner layers can include at least 80 wt % of a propylene-based polymer. The one or more inner layers can include at least 90 wt % of a propylene-based polymer. The one or more inner layers can include at least 95 wt % of a propylene-based polymer.

In one or more embodiments, the one or more inner layers include from about 2 to about 30 wt % of the one or more slip agents. In one or more embodiments, the one or more inner layers include from about 0.2 wt % to about 20 wt % of the one or more slip agents. In one or more embodiments, the one or more inner layers include from about 0.2 wt % to about 10 wt % of the one or more slip agents. In one or more embodiments, the one or more inner layers include from about 0.2 wt % to about 5 wt % of the one or more slip agents. In one or more embodiments, the one or more inner layers include the one or more slip agents in an amount ranging from a low of about 0.2 wt %, 0.5 wt % or 1 wt % to a high of about 2 wt %, 5 wt % or 10 wt %.

In one or more embodiments, the one or more inner layers include from about 2 to about 30 wt % of the one or more hydrocarbon resins. In one or more embodiments, the one or more inner layers include from about 0.2 wt % to about 20 wt % of the one or more hydrocarbon resins. In one or more embodiments, the one or more inner layers include from about 0.2 wt % to about 10 wt % of the one or more hydrocarbon resins. In one or more embodiments, the one or more inner layers include from about 0.2 wt % to about 5 wt % of the one or more hydrocarbon resins. In one or more embodiments, the one or more inner layers include the one or more hydrocarbon resins in an amount ranging from a low of about 0.2 wt %, 0.5 wt % or 1 wt % to a high of about 2 wt %, 5 wt % or 10 wt %.

In one or more embodiments, the inner layer or facing layer blend can contain additional additives, which can be introduced at the same time as the other components or later in time, or later downstream in the case of using an extruder or Buss kneader. Examples of such additives are antioxidants, antiblocking agents, antistatic agents, ultraviolet stabilizers, foaming agents, and processing aids. Such additives can comprise from about 0.1 to about 10 percent by weight of the blend based on the total weight of blend. The additives can be added to the blend in pure form or in master batches.

Articles

The nonwoven fabric can be used for a variety of articles including consumer and industrial goods. Illustrative consumer articles include but are not limited to incontinence pads, disposable diapers, training pants, clothing, undergarments, sports apparel, face masks, gowns, and filtration media.

Preferably, the nonwoven fabric is layered with one or more facing layers thermally bonded to one or more inner layers. Each layer can be either spunbonded or meltblown to from a single fabric layer. Accordingly, the layered nonwoven fabric can include numerous combinations of spunbonded (S) and meltblown (M) layers including but not limited to spunbond-spunbond (SS), spunbond-meltblown-spunbond (SMS), spunbond-spunbond-spunbond (SSS), spunbond-meltblown-meltblown-spunbond (SMMS) spunbond-spunbond-spunbond-spunbond (SS-SS), spunbond-meltblown or vice versa (SM or MS), spunbond-meltblown-spunbond-spunbond-meltblown-spunbond (SMS-SMS), spunbond-meltblown-spunbond-spunbond-meltblown-spunbond (SMMS-SMMS) arrangements, as well as other combinations and variations of the foregoing. The multiple fabric layers are then bonded together by the application of heat and pressure to form the desired fabric composite. The spunbonded fabric layers can be prebonded by heated press rolls, providing structural integrity to the fabric.

Melt blown fabrics are generally webs of fine filaments having a fiber diameter in the range of from 0.1 to 20 microns. Typical fiber diameters for melt blown fabrics are in the range of from 1 to 10 microns, or from 1 to 5 microns. The nonwoven webs formed by these fine fiber diameters have very small pore sizes and can, therefore, have excellent barrier properties.

The meltblown layers can be prepared by extruding the blend in molten form through a plurality of fine, usually circular capillaries of a die. A high-velocity, usually heated gas (e.g., air) stream attenuates the filaments of molten thermoplastic material to reduce their diameter. Thereafter the meltblown fibers, which include any melt processable additives that were present in the blend, are carried by the high-velocity heated gas stream and are deposited on a collecting surface to form a nonwoven web of randomly dispersed meltblown fibers.

The spunbonded layers can be produced by continuously extruding the blend through a plurality of fine, usually circular capillaries of a spinnerette having typically 1000 holes per meter length, or with banks of smaller spinnerets, with each spinneret section containing as few as 40 holes. After exiting the spinneret, the molten fibers are quenched by a cross-flow air quench system, then pulled away from the spinneret and attenuated (drawn) by high speed air. The friction between the flowing air and the filaments creates a force which draws the filaments, i.e., attenuates the filaments to a smaller diameter. The filaments are drawn to achieve molecular orientation and tenacity. The continuous filaments are then deposited in a substantially random manner to form a web of substantially continuous and randomly arranged, molecularly oriented filaments. The web is then passed through compaction rolls and then between heated calender rolls where the raised lands on one roll bond the web at points covering 10% to 40% of its area to form a nonwoven fabric. The top calender roll can have an embossed pattern while the bottom roll is smooth.

In one or more embodiments, any one of the one or more facing layers and the one or more inner layers can be a multicomponent layer. The term "multicomponent" as used herein, refers to fibers which have been formed from at least two polymers extruded from separate extruders and meltblown or spun together to form one fiber. Multicomponent fibers are also referred to in the art as bicomponent fibers. The polymers used in multicomponent fibers are typically different from each other; however, conjugated fibers can be monocomponent fibers. The polymers can be arranged in distinct zones across the cross-section of the conjugated fibers and extend continuously along the length of the conjugated fibers. The configuration of conjugated fibers can be, for example, a sheath/inner arrangement wherein one polymer is surrounded by another, a side by side arrangement, a pie arrangement or an "islands-in-the-sea" arrangement. Conjugated fibers are described in U.S. Pat. Nos. 5,108,820; 5,336,552; and 5,382,400; the entire disclosures of which are hereby incorporated herein by reference. In a particular embodiment, the fibers can be part of a conjugated configuration.

In one or more embodiments, the fibers can be in the form of continuous filament yarn, partially oriented yarn, and staple fibers. Continuous filament yarns typically range from 40 denier to 20,000 denier (denier=number of grams per 9000 yards). Filaments currently range from 1 to 20 or more denier per filament (dpf). Spinning speeds are typically 800 m/min to 1500 m/min (2500 ft/min to 5000 ft/min).

Partially oriented yarn (POY) is the fiber produced directly from fiber spinning without solid state drawing, as in the continuous filament. The orientation of the molecules in the fiber is done in the melt state just after the molten polymer leaves the spinneret.

Staple fiber filaments can range, for example, from 1.5 dpf to 70 dpf or more, depending on the application. There are two basic staple fiber fabrication processes: traditional and compact spinning. The traditional process typically involves two steps: 1) producing, applying, finishing, and winding, followed by 2) drawing, a secondary finish application, crimping, and cutting into the staple.

In some embodiments, the fabrics can be further processed. For example, the fabric can be subjected to a surface treatment process, such as sizing. Thus, in some embodiments, the fabric can contain sizing additives such as rosins, resins, or waxes. As another example, the fabric can be subjected to a tentering process. In one or more embodiments above, blocking agents can be added to the fabric in a processing step subsequent to the formation of the fabric.

Definitions and Test Methods

For purposes of convenience, various definitions and specific test procedures are identified below. However, when a person of ordinary skill reads this patent and wishes to determine whether a composition or polymer has a particular property identified in a claim, then any published or well-recognized method or test procedure can be followed to determine that property, although the specifically identified procedure is preferred. Each claim should be construed to cover the results of any of such procedures, even to the extent different procedures may yield different results or measurements. Thus, a person of ordinary skill in the art is to expect experimental variations in measured properties that are reflected in the claims. All numerical values can be considered to be "about" or "approximately" the stated value, in view of the nature of testing in general.

Comonomer content: The comonomer content and sequence distribution of the polymers can be measured using $^{13}C$ nuclear magnetic resonance (NMR) by methods well known to those skilled in the art. Comonomer content of discrete molecular weight ranges can be measured using methods well known to those skilled in the art, including Fourier Transform Infrared Spectroscopy (FTIR) in conjunction with samples by GPC, as described in Wheeler and Willis, Applied Spectroscopy, 1993, vol. 47, pp. 1128-1130.

In the particular case of propylene-ethylene copolymers containing greater than 75 wt % propylene, the comonomer content can be measured as follows. A thin homogeneous film is pressed at a temperature of about 150° C. or greater, and mounted on a Perkin Elmer PE 1760 infrared spectrophotometer. A full spectrum of the sample from 600 cm$^{-1}$ to 4000 cm$^{-1}$ is recorded and the monomer weight percent of ethylene can be calculated according to the following equation: Ethylene wt %=82.585-111.987X+30.045X$^2$, where X is the ratio of the peak height at 1155 cm$^{-1}$ and peak height at either 722 cm$^{-1}$ or 732 cm$^{-1}$, whichever is higher.

Polyene content: The amount of polyene present in a polymer can be inferred by the quantitative measure of the amount of the pendant free olefin present in the polymer after polymerization. Several procedures such as iodine number and the determination of the olefin content by H$^1$ or $^{13}C$ nuclear magnetic resonance (NMR) have been established. In embodiments described herein where the polyene is ENB, the amount of polyene present in the polymer can be measured using ASTM D3900.

Isotactic: The term "isotactic" is defined herein as a polymer sequence in which greater than 50% of the pairs of pendant methyl groups located on adjacent propylene units, which are inserted into the chain in a regio regular 1,2 fashion and are not part of the backbone structure, are located either above or below the atoms in the backbone chain, when such atoms in the backbone chain are all in one plane. Certain combinations of polymers in blends or polymer sequences within a single polymer are described as having "substantially the same tacticity," which herein means that the two polymers are both isotactic according to the definition above.

Tacticity: The term "tacticity" refers to the stereoregularity of the orientation of the methyl residues from propylene in a polymer. Pairs of methyl residues from contiguous propylene units identically inserted which have the same orientation with respect to the polymer backbone are termed "meso" (m). Those of opposite configuration are termed "racemic" (r). When three adjacent propylene groups have methyl groups with the same orientation, the tacticity of the triad is 'mm'. If two adjacent monomers in a three monomer sequence have the same orientation, and that orientation is different from the relative configuration of the third unit, the tacticity of the triad is 'mr'. When the middle monomer unit has an opposite configuration from either neighbor, the triad has 'rr' tacticity. The fraction of each type of triad in the polymer can be determined and when multiplied by 100 indicates the percentage of that type found in the polymer.

The triad tacticity of the polymers described herein can be determined from a $^{13}C$ nuclear magnetic resonance (NMR) spectrum of the polymer as described below and as described in U.S. Pat. No. 5,504,172, the disclosure of which is hereby incorporated herein by reference.

Tacticity Index: The tacticity index, expressed herein as "m/r", is determined by $^{13}C$ nuclear magnetic resonance (NMR). The tacticity index m/r is calculated as defined in H. N. Cheng, Macromolecules, 17, 1950 (1984). An m/r ratio of 1.0 generally describes a syndiotactic polymer, and an m/r ratio of 2.0 generally describes an atactic material. An isotactic material theoretically can have a ratio approaching infinity, and many by-product atactic polymers have sufficient isotactic content to result in ratios of greater than 50.

Melting point and heat of fusion: The melting point (TM) and heat of fusion of the polymers described herein can be determined by Differential Scanning Calorimetry (DSC), using the ASTM E-794-95 procedure. About 6 to 10 mg of a sheet of the polymer pressed at approximately 200° C. to 230° C. and allowed to cool by hanging in air under ambient conditions, is removed with a punch die and annealed at room temperature for 48 hours. At the end of this period, the sample is placed in a Differential Scanning Calorimeter (Perkin Elmer Pyris 1 Thermal Analysis System) and cooled to about −50° C. to −70° C. The sample is heated at about 20° C./min to attain a final temperature of about 180° C. to 200° C. The term "melting point," as used herein, is the highest peak among principal and secondary melting peaks as determined by DSC, discussed above. The thermal output is recorded as the area under the melting peak of the sample, which is typically at a maximum peak at about 30° C. to about 175° C. and occurs between the temperatures of about 0° C. and about 200° C. The thermal output is measured in Joules as a measure of the heat of fusion. The melting point is recorded as the temperature of the greatest heat absorption relative to a baseline measurement within the range of melting of the sample.

Molecular weight and molecular weight distribution: The molecular weight and molecular weight distribution of the polymers described herein can be measured as follows. Molecular weight distribution (MWD) is a measure of the range of molecular weights within a given polymer sample. It is well known that the breadth of the MWD can be characterized by the ratios of various molecular weight averages, such as the ratio of the weight average molecular weight to the number average molecular weight, Mw/Mn, or the ratio of the Z-average molecular weight to the weight average molecular weight Mz/Mw.

Mz, Mw, and Mn can be measured using gel permeation chromatography (GPC), also known as size exclusion chromatography (SEC). This technique utilizes an instrument containing columns packed with porous beads, an elution solvent, and detector in order to separate polymer molecules of different sizes. In a typical measurement, the GPC instrument used is a Waters chromatograph equipped with ultrastyrogel columns operated at 145° C. The elution solvent used is trichlorobenzene. The columns are calibrated using sixteen polystyrene standards of precisely known molecular weights. A correlation of polystyrene retention volume obtained from the standards, to the retention volume of the polymer tested yields the polymer molecular weight.

Average molecular weights M can be computed from the expression:

$$M = \frac{\sum_i N_i M_i^{n+1}}{\sum_i N_i M_i^n}$$

where Ni is the number of molecules having a molecular weight Mi. When n=0, M is the number average molecular weight, Mn. When n=1, M is the weight average molecular weight, Mw. When n=2, M is the Z-average molecular weight, Mz. The desired MWD function (e.g., Mw/Mn or Mz/Mw) is the ratio of the corresponding M values. Measurement of M and MWD is well known in the art and is discussed in more detail in, for example, Slade, P. E. Ed., Polymer Molecular Weights Part II, Marcel Dekker, Inc., NY, (1975) 287-368; Rodriguez, F., Principles of Polymer Systems $3^{rd}$ ed., Hemisphere Pub. Corp., NY, (1989) 155-160; U.S. Pat. No. 4,540,753; Verstrate et al., Macromolecules, vol. 21, (1988) 3360; and references cited therein.

Mooney viscosity: Mooney viscosity, as used herein, is measured as ML(1+4)@ 125° C. according to ASTM D1646.

Melt flow rate and melt index: The determination of the Melt Flow rate (MFR) and the Melt Index of the polymer is according to ASTM D1238 using modification 1 with a load of 2.16 kg. In this version of the method, a portion of the sample extruded during the test was collected and weighed. The sample analysis is conducted at 230° C. with a 1 minute preheat on the sample to provide a steady temperature for the duration of the experiment. This data, expressed as dg of sample extruded per minute (or g/10 min.), is indicated as MFR. In an alternative procedure, the test is conducted in an identical fashion except at a temperature of 190° C. This data is referred to as MI@190 C.

Isotacticity Index: The isotacticity index is calculated according to the procedure described in EP 0374695A2. The IR spectra of a thin film of the material is recorded and the absorbance at 997 $cm^{-1}$ and the absorbance at 973 cm-1 are determined. The quotient of the absorbance at 997 $cm^{-1}$ to the absorbance at 973 $cm^{-1}$ is multiplied by 100 to yield the isotacticity index. In the determination of the absorbance at these two positions, the position of zero absorbance is the absorbance when there is no analytical sample present in the sample beam.

EXAMPLES

The foregoing discussion can be further described with reference to the following non-limiting examples. The examples illustrate the effects of an inelastic facing layer according to one or more embodiments described laminated to an elastic inner layer. Surprisingly, the facing layers exhibited a dry touch and had a minimal detrimental effect on the elastic properties of the elastic inner layer. Moreover, the facing layers adhered well to the inside layer without delimitation, and exhibited excellent mechanical properties, especially tensile strength and elasticity.

Facing Layer

The facing layer contained a polypropylene resin, Escorene PP 3546G (from ExxonMobil Chemical), and was constructed in a meltblown process. The polypropylene resin ("MBPP") had a nominal MFR of 1,200 g/10 min. A 500 mm Reifenhäuser melt blowing pilot line equipped with a bicomponent side by side die was used for making the facing layer. The bicomponent features of the die were not utilized, since the same PP resin was introduced into both extruders A and B respectively. The process conditions were as follows:

Extruder Speed: 18 rpm
Extruder Temperature (last zone): 260° C.
Spin pump: 2.8 rpm
Melt Temperature Spin Pump: 250° C.
Melt temperature Die Tip: 254° C.
Pressure in front of Die: 0.069 MPa
Die to Collector Distance (DCD): 177 mm
Air Temperature: 260° C.
Suction Blower: 2005 rpm
Air Rate: 350 scfm
Spin Belt: 28.1 m/min
Winder: 2.87 m/min
Basis Weight: ~5 gsm A 1,000 m roll of the PP nonwoven fabric was produced and will be referred to as MBPP.

Elastic Layer

The elastic layer was spunbond using different propylene-based copolymers (POLYMERS 1-4) as shown in Table A. The propylene-based copolymers (POLYMERS 1-4) each have 60 wt % or more units derived from propylene, and isotactically arranged propylene derived sequences.

TABLE A

| Propylene-based copolymers | | | |
|---|---|---|---|
| Propylene-based copolymers | Melt Flow Rate @ 230° C. (g/10 min) | Density (g/cm³) | Heat of Fusion, J/g |
| POLYMER 1 | 80 | 0.865 | 21 |
| POLYMER 2 | 80 | 0.868 | 25 |
| POLYMER 3 | 80 | 0.859 | 12 |
| POLYMER 4 | 3 | 0.855 | 6 |

When modified, POLYMERS 1-4 were modified in-line through the addition of a slip agent and in some cases, a hydrocarbon resin. The slip agent was a melt blend of Erucamide (30 wt. %) and POLYMER 1 (70 wt. %), pelletized for in line addition in the side feeder or extruder hopper. The hydrocarbon resin, when used, was PA-609, commercially available from ExxonMobil Chemical, and added in stable pellet form.

POLYMERS 1 to 4, mixed with additives, were converted into nonwoven fabrics in a spunbond process using a 1 meter Reifenhauser Reicofil® 1.5 equipment. The surface modifying additives were introduced in line through side feeders. The extruder temperature profile was adjusted to provide a melt temperature of 209° C. The output was maintained either at 0.2 ghm (grams/hole/min) or at 0.3 ghm by suitably adjusting the spin pump rpm. The draw force, represented by the quench blower rpm, was adjusted to the maximum, a condition where the fibers spin without drips and provide a uniform web on the forming belt. Samples were also produced at 70% of the maximum draw force to change the fiber diameter.

The fabrics were tested for tensile and elastic properties using a 25.4 mm width specimen. At least five samples were tested for each composition in both the machine direction (MD) and the cross direction (CD). The average values from testing of multiple specimens were used in the analysis and representation of the test data. Various attributes used in defining the elastic parameters follows:

Permanent Set (%): Strain level corresponding to zero force on return, upon stretching a non woven fabric to 100% extension. This can be done either in the machine direction or the transverse direction.

Load Loss (%) (LL): (Load on Ascending Curve—Load on Descending Curve)/Load on Ascending calculated at the 50% strain level.

Hysteresis (lb-in/in): Area enclosed by the ascending and descending portion of the load displacement curve.

Mechanical Hysteresis (lb-in/in) (MH): Area under the ascending portion of the load displacement curve.

Hysteresis (%): Hysteresis/Mechanical Hysteresis.

PS: Pre stretch to 100% strain.

Table 1 shows the compositions, process conditions and properties for nonwoven fabrics from POLYMER 1 that were modified with slip and/or PA 609. Table 1A shows the elastic properties of the compositions of Table 1. The tensile values correspond to peak load and peak strain. The tensile load was calculated by dividing the load by the width of the sample (gm/cm).

Comparative Example 1 (C1) did not include a meltblown PP facing layer, while Examples 2, 3 and 5 each contained a MBPP layer. Comparative Example 4 (C4) corresponds to a formulation containing slip (2%) and POLYMER 4 (10%).

The MBPP was introduced as a carrier web and thermally bonded to the elastic facing nonwoven. The bonding was accomplished in a calender at a bond temperature of 74° C. The elastic layer of Example 2 contained 2 wt % slip masterbatch, while the elastic layer of Example 3 contained 2% slip and 10% PA 609.

As seen from Table 1, the composite laminate examples displayed reasonable elongation relative to the Comparative Example 1 (C1), and possessed a facing layer that was devoid of modifying additives. The addition of the inelastic PP facing layer (MBPP) produced only a marginal increase in permanent set (Example 2 vs C1). The thermal bonding of the facing layer to the elastic web precluded any delamination at the interface on being stretched to failure.

7 and 8 contained the additional MBPP facing layer. In example 8, the draw force was decreased to 70% of maximum to increase the fiber diameter and enhance the elongation of the elastic substrate. As seen in Table 2, peak elongation was enhanced in Example 8 (194%) compared to Example 7 (156%).

Comparative Example 9 (C9) shows the properties of POLYMER 2 fabric with 2% slip and 10% PA 609. Example 10 is the corresponding analog with the MBPP facing layer. Comparative Example 11 (C11) and Example 12 represent similar fabrics produced at a reduced draw force. The fabrics possessing the MBPP facing layer had high elongation (>150%) and an adhesion enabling layer with an acceptable dry feel.

Example 12 shows the fabric of the same composition as C4, with the facing layer. The addition of POLYMER 4 enhanced the tensile strength notably in the MD direction relative to Example 2.

Table 3 shows the composition, process conditions and properties for nonwoven fabrics containing POLYMER 3 and modified with slip and optionally PA 609 additive. Table 3A shows the elastic properties. Example 14 containing the MBPP facing layer showed high CD elongation (216%).

Table 4A shows the composition of nonwoven fabrics in which the facing layer was a blend of POLYMER 1 and PP homopolymer of varying melt flow rate. The facing layer nonwoven was fabricated to a constant basis weight of 17 gsm as either un-bonded or lightly bonded using minimum pressure. In a second step, the elastic layer that included POLYMER 1 modified with slip was applied as a spunbond layer over the facing layer, and the composite was calendered at a

TABLE 1

Nonwoven Fabrics Compositions

| | COMPOSITION | | | | PROCESS | | | | FABRIC PROPERTIES | | Elong | Elong |
|---|---|---|---|---|---|---|---|---|---|---|---|---|
| Example | Polymer | Slip (%) | PA 609 (%) | POLYMER 4 (%) | Calender Temp (C.) | GHM | Melt Temp Die (C.) | Quench Blower Speed (RPM) | Basis Weight (gsm) | Tens Pk MD (gm/cm) | Tens Pk CD (gm/cm) | Pk MD (%) | Pk CD (%) |
| C1 | POLYMER 1 | 2 | | | 74 | 0.2 | 209 | 2096 | 48.6 | 406 | 193 | 191 | 248 |
| 2 | POLYMER 1 + MB PP | 2 | | | 74 | 0.2 | 209 | 2096 | 48.6 | 379 | 213 | 162 | 161 |
| 3 | POLYMER 1 + MB PP | 2 | 10 | | 74 | 0.25 | 210 | 2206 | 50 | 437 | 285 | 194 | 200 |
| C4 | POLYMER 1 | 2 | | 10 | 74 | 0.2 | 210 | 2102 | 52 | 471 | 234 | 213 | 274 |
| 5 | POLYMER 1 + MB PP | 2 | | 10 | 74 | 0.2 | 210 | 2102 | 52 | 467 | 229 | 177 | 172 |

TABLE 1A

Elastic Properties of Nonwoven Fabrics of Table 1

| | COMPOSITION | | | | Perm Set MD (%) | Perm Set CD (%) | Set PS MD (%) | Set PS CD (%) | | | LL PS MD | LL PS CD | | | MH PS MD | |
|---|---|---|---|---|---|---|---|---|---|---|---|---|---|---|---|---|
| Example | Polymer | Slip (%) | PA 609 (%) | POLYMER 4 (%) | | | | | LL MD | LL CD | | | MH MD | MH CD | | MH PS CD |
| C1 | POLYMER 1 | 2 | | | 18 | 18 | 16 | 13 | 83 | 80 | 68 | 64 | 79 | 75 | 70 | 54 |
| 2 | POLYMER 1 + MB PP | 2 | | | 21 | 22 | 19 | 17 | 91 | 92 | 75 | 74 | 86 | 85 | 77 | 74 |
| 3 | POLYMER 1 + MB PP | 2 | 10 | | 30 | 30 | 28 | 26 | 96 | 95 | 88 | 87 | 86 | 87 | 74 | 77 |
| C4 | POLYMER 1 | 2 | | 10 | 18 | 13 | 13 | 13 | 81 | 79 | 66 | 61 | 77 | 66 | 68 | 64 |
| 5 | POLYMER 1 + MB PP | 2 | | 10 | 18 | 20 | 17 | 17 | 89 | 90 | 70 | 69 | 85 | 85 | 74 | 76 |

Table 2 shows the composition, process conditions and properties for nonwoven fabrics containing POLYMER 2 and modified with slip and optionally PA 609 additive. Table 2A displays the elastic properties of the fabrics in Table 2. Comparative Example 6 (C6) contained 2% slip, while Examples temperature of 72° C. The basis weight of the elastic layer was either 55 gsm or 86 gsm, to provide a composite laminate of 73 or 103 gsm total basis weight. Example 29 illustrates a construction having a meltblown layer of PP applied as a facing layer to the elastic laminate having POLYMER 1.

TABLE 2

Nonwoven Fabrics Compositions of POLYMER 2

| | COMPOSITION | | | PROCESS | | | | Quench | FABRIC PROPERTIES | | | | |
|---|---|---|---|---|---|---|---|---|---|---|---|---|---|
| Example | Polymer | Slip (%) | PA 609 (%) | Calender Temp (C.) | GHM | Melt Temp Die (C.) | Blower Speed (RPM) | | Basis Weight (gsm) | Tens Pk MD (gm/cm) | Tens Pk CD (gm/cm) | Elong Pk MD (%) | Elong Pk CD (%) |
| C6 | POLYMER 2 | 2 | | 74 | 0.2 | 211 | 2000 | | 60 | 868 | 476 | 192 | 207 |
| 7 | POLYMER 2 + MB PP | 2 | | 74 | 0.2 | 211 | 2003 | | 60 | 746 | 422 | 156 | 174 |
| 8 | POLYMER 2 + MB PP | 2 | | 74 | 0.2 | 211 | 1605 | | 60 | 528 | 274 | 194 | 180 |
| C9 | POLYMER 2 | 2 | 10 | 74 | 0.3 | 211 | 1996 | | 62 | 519 | 419 | 210 | 217 |
| 10 | POLYMER 2 + MB PP | 2 | 10 | 74 | 0.3 | 211 | 1999 | | 62 | 463 | 335 | 201 | 207 |
| C11 | POLYMER 2 | 2 | 10 | 74 | 0.3 | 211 | 1708 | | 62 | 474 | 347 | 239 | 267 |
| 12 | POLYMER 2 + MB PP | 2 | 10 | 74 | 0.3 | 211 | 1718 | | 62 | 426 | 259 | 197 | 156 |

TABLE 2A

Elastic Properties of Nonwoven Fabrics of Table 2

| | COMPOSITION | | | ELASTIC PROPERTIES | | | | | | | | | | | |
|---|---|---|---|---|---|---|---|---|---|---|---|---|---|---|---|
| Example | Polymer | Slip (%) | PA 609 (%) | Perm Set MD (%) | Perm Set CD (%) | Set PS MD (%) | Set PS CD (%) | LL MD | LL CD | LL PS MD | LL PS CD | MH MD | MH CD | MH PS MD | MH PS CD |
| C6 | POLYMER 2 | 2 | | 29 | 24 | 23 | 22 | 92 | 91 | 85 | 82 | 86 | 83 | 80 | 78 |
| 7 | POLYMER 2 + MBPP | 2 | | 28 | 28 | 25 | 28 | 94 | 94 | 84 | 86 | 88 | 82 | 80 | 82 |
| 8 | POLYMER 2 + MBPP | 2 | | 25 | 26 | 22 | 26 | 93 | 94 | 81 | 86 | 87 | 88 | 79 | 82 |
| C9 | POLYMER 2 | 2 | 10 | 37 | 36 | 33 | 33 | 97 | 96 | 92 | 92 | 87 | 87 | 81 | 80 |
| 10 | POLYMER 2 + MBPP | 2 | 10 | 31 | 32 | 26 | 26 | 96 | 96 | 87 | 88 | 87 | 84 | 70 | 81 |
| C11 | POLYMER 2 | 2 | 10 | 28 | 27 | 24 | 24 | 93 | 92 | 84 | 81 | 84 | 83 | 74 | 89 |
| 12 | POLYMER 2 + MBPP | 2 | 10 | 30 | 31 | 26 | 26 | 95 | 96 | 87 | 86 | 88 | 88 | 81 | 71 |

TABLE 3

Nonwoven Fabrics from POLYMER 3

| | COMPOSITION | | PROCESS | | | | Quench | FABRIC PROPERTIES | | | | |
|---|---|---|---|---|---|---|---|---|---|---|---|---|
| Example | Polymer | Slip (%) | Calender Temp (C.) | GHM | Melt Temp Die (C.) | Blower Speed (RPM) | | Basis Weight (gsm) | Tens Pk MD (gm/cm) | Tens Pk CD (gm/cm) | Elong Pk MD (%) | Elong Pk CD (%) |
| C13 | POLYMER 3 | 2 | 74 | 0.2 | 211 | 2011 | | 59.8 | 497 | 268 | 252 | 282 |
| 14 | POLYMER 3 + MB PP | 2 | 74 | 0.2 | 211 | 1997 | | 59.8 | 489 | 272 | 182 | 216 |

TABLE 3A

Elastic Properties of Nonwoven Fabrics of Table 3

| | COMPOSITION | | ELASTIC PROPERTIES | | | | | | | | | | | |
|---|---|---|---|---|---|---|---|---|---|---|---|---|---|---|
| Example | Polymer | Slip (%) | Perm Set MD (%) | Perm Set CD (%) | Set PS MD (%) | Set PS CD (%) | LL MD | LL CD | LL PS MD | LL PS CD | MH MD | MH CD | MH PS MD | MH PS CD |
| C13 | POLYMER 3 | 2 | 18 | 17 | 15 | 14 | 82 | 82 | 67 | 62 | 79 | 65 | 68 | 66 |
| 14 | POLYMER 3 + MB PP | 2 | 19 | 22 | 16 | 18 | 89 | 91 | 69 | 73 | 84 | 83 | 69 | 61 |

TABLE 4A

Composition of Nonwoven Composite Laminates Containing POLYMER 1/PP Facing layer

| | SB ELASTIC SUBSTRATE | | FACING LAYER CONSTRUCTION | | | | | CONSTRUCTION | | | |
|---|---|---|---|---|---|---|---|---|---|---|---|
| Example | Polymer | Slip (%) | Type | Polymer 1 (%) | PP (%) | PP MFR | Facing Layer Bonding | Elastic Layer (gsm) | Facing Layer (gsm) | Facing Layer (%) | Total Basis(gsm) |
| 15 | Polymer 1 | 2 | SB | 50 | 50 | 36 | min pli | 55 | 17 | 24 | 73 |
| 16 | Polymer 1 | 2 | SB | 50 | 50 | 36 | min pli | 86 | 17 | 17 | 103 |
| 17 | Polymer 1 | 2 | SB | 50 | 50 | 400 | min pli | 55 | 17 | 24 | 73 |
| 18 | Polymer 1 | 2 | SB | 50 | 50 | 400 | min pli | 86 | 17 | 17 | 103 |
| 19 | Polymer 1 | 2 | SB | 50 | 50 | 1500 | min pli | 55 | 17 | 24 | 73 |
| 20 | Polymer 1 | 2 | SB | 50 | 50 | 1500 | min pli | 86 | 17 | 17 | 103 |
| 21 | Polymer 1 | 2 | SB | 75 | 25 | 36 | open | 55 | 18 | 24 | 73 |
| 22 | Polymer 1 | 2 | SB | 75 | 25 | 36 | open | 86 | 18 | 17 | 103 |
| 23 | Polymer 1 | 2 | SB | 75 | 25 | 400 | open | 55 | 18 | 24 | 73 |
| 23 | Polymer 1 | 2 | SB | 75 | 25 | 400 | open | 86 | 18 | 17 | 104 |
| 25 | Polymer 1 | 2 | SB | 75 | 25 | 800 | open | 55 | 18 | 24 | 73 |
| 26 | Polymer 1 | 2 | SB | 75 | 25 | 800 | open | 86 | 18 | 17 | 103 |
| 27 | Polymer 1 | 2 | SB | 75 | 25 | 1500 | open | 55 | 18 | 24 | 73 |
| 28 | Polymer 1 | 2 | SB | 75 | 25 | 1500 | open | 86 | 18 | 17 | 103 |
| 29 | Polymer 1 | 2 | MB | 0 | 100 | 1500 | none | 70 | 5 | 7 | 75 |
| C 30 | Polymer 1 Monolayer | 2 | None | | | | min pli | 71 | 0 | 0 | 71 |

Table 4B shows the composition properties of nonwoven fabrics corresponding to the composition shown in TABLE 4A. The facing layer formulations containing a high melt flow rate PP (Examples 23, 24, 26 and 28) provided a higher elongation in the composite nonwoven. A tactile touch was observed at the POLYMER 1/PP blend ratio of 75/25. Compared to the monolayer Comparative Example 30 (C30), all Examples that contain the POLYMER 1/PP facing layer exhibit a dry touch. Furthermore, Examples 23, 24 and 26 showed higher elongation in the cross direction compared to the control example at a temperature of 72° C.

Table 5A shows the composition of nonwoven fabrics in which the facing layer was a blend of POLYMER 2 and PP homopolymer of varying melt flow rate. The facing layer nonwoven was fabricated to a constant basis weight of 17 gsm as either un-bonded or lightly bonded using minimum pressure. In a second step, the elastic layer that included POLYMER 2 modified with slip was applied as a spunbond layer over the facing layer, and the composite was calendered at a temperature of 72° C. The basis weight of the elastic layer was 53 gsm to provide a composite laminate of 70 gsm total basis weight.

TABLE 4B

Properties of Nonwoven Composite Laminates Containing POLYMER 1/PP Facing layer

| Example | Tens Pk MD (gm/cm) | Tens Pk CD (gm/cm) | Elong Pk MD (%) | Elong Pk CD (%) | Perm Set MD (%) | Perm Set CD (%) | Set PS MD (%) | Set PS CD (%) |
|---|---|---|---|---|---|---|---|---|
| 15 | 696 | 460 | 106 | 138 | 24 | 30 | 20 | 28 |
| 16 | 748 | 617 | 106 | 165 | 38 | 30 | 33 | 28 |
| 17 | 569 | 383 | 152 | 173 | 34 | 29 | 30 | 26 |
| 18 | 811 | 573 | 177 | 245 | 28 | 26 | 27 | 24 |
| 19 | 523 | 410 | 129 | 166 | 30 | 29 | 26 | 26 |
| 20 | 771 | 571 | 161 | 209 | 30 | 32 | 28 | 27 |
| 21 | 494 | 354 | 135 | 211 | 30 | 27 | 24 | 26 |
| 22 | 698 | 489 | 176 | 230 | 33 | 27 | 30 | 24 |
| 23 | 614 | 387 | 175 | 262 | 29 | 22 | 27 | 22 |
| 23 | 744 | 526 | 197 | 281 | 28 | 25 | 26 | 22 |
| 25 | 619 | 358 | 164 | 245 | 30 | 24 | 28 | 20 |
| 26 | 768 | 573 | 189 | 271 | 28 | 22 | 23 | 18 |
| 27 | 607 | 338 | 162 | 220 | 29 | 24 | 20 | 20 |
| 28 | 449 | 548 | 185 | 285 | 27 | 25 | 24 | 22 |
| 29 | 335 | 215 | 166 | 183 | 26 | 23 | 22 | 22 |
| C 30 | 363 | 243 | 218 | 250 | 20 | 20 | 16 | 18 |

TABLE 5A

Composition of Nonwoven Composite Laminates Containing POLYMER 1/PP Facing layer

| | SB ELASTIC SUBSTRATE | | FACING LAYER CONSTRUCTION | | | | CONSTRUCTION | | | |
|---|---|---|---|---|---|---|---|---|---|---|
| Example | Polymer | Slip (%) | Type | Polymer 1 (%) | PP (%) | PP MFR | Facing Layer Bonding | Elastic Layer (gsm) | Facing Layer (gsm) | Facing Layer (%) | Total Basis (gsm) |
| 31 | Polymer 2 | 2 | SB | 50 | 50 | 36 | min pli | 53 | 17 | 25 | 70 |
| 32 | Polymer 2 | 2 | SB | 50 | 50 | 36 | min pli | 53 | 17 | 25 | 70 |
| 33 | Polymer 2 | 2 | SB | 50 | 50 | 1500 | min pli | 53 | 17 | 25 | 70 |
| 34 | Polymer 2 | 2 | SB | 50 | 50 | 1500 | min pli | 53 | 17 | 25 | 70 |
| 35 | Polymer 2 | 2 | SB | 75 | 25 | 36 | open | 53 | 18 | 25 | 71 |
| 36 | Polymer 2 | 2 | SB | 75 | 25 | 36 | open | 53 | 18 | 25 | 71 |
| 37 | Polymer 2 | 2 | SB | 75 | 25 | 400 | open | 53 | 18 | 25 | 71 |
| 38 | Polymer 2 | 2 | SB | 75 | 25 | 400 | open | 53 | 18 | 25 | 71 |

* unless otherwise specified all tensile are based on 1 in width.

Table 5B shows the composition properties of nonwoven fabrics corresponding to the compositions shown in Table 5A. The facing layer formulations containing a high melt flow rate PP (Examples 37 and 38) provided a higher elongation in the composite nonwoven. A tactile touch was observed at the POLYMER 2/PP blend ratio of 75/25 in the facing layer, while the other layer exhibited a feel typical of the presence of slip additive.

TABLE 5B

Properties of Nonwoven Composite Laminates Containing POLYMER 1/PP Facing layer

| Example | Tens Pk MD (gm/cm) | Tens Pk CD (gm/cm) | Elong Pk MD (%) | Elong Pk CD (%) | Perm Set MD (%) | Perm Set CD (%) | Set PS MD (%) | Set PS CD (%) |
|---|---|---|---|---|---|---|---|---|
| 31 | 864 | 603 | 96 | 136 | 38 | 37 | 38 | 36 |
| 32 | 630 | 392 | 91 | 114 | 45 | 36 | 42 | 33 |
| 33 | 734 | 471 | 121 | 143 | 42 | 36 | 36 | 33 |
| 34 | 465 | 354 | 117 | 165 | 34 | 38 | 36 | 36 |
| 35 | 773 | 435 | 129 | 159 | 40 | 34 | 40 | 32 |
| 36 | 531 | 367 | 123 | 191 | 38 | 33 | 33 | 30 |
| 37 | 814 | 363 | 155 | 178 | 36 | 28 | 32 | 26 |
| 38 | 562 | 379 | 165 | 218 | 32 | 30 | 29 | 24 |

Specific embodiments of the invention further include:
1. A nonwoven fabric, comprising:
   one or more facing layers thermally bonded to one or more inner layers, wherein:
   the facing layers are inelastic or partially elastic nonwoven webs comprising one or more propylene-based polymers, the facing layer having a permanent set above 30%;
   the inner layers are elastic nonwoven webs comprising one or more propylene-based polymers and one or more slip agents, the inner layer having a permanent set below 28%; and
   the one or more propylene-based polymers have (i) 60 wt % or more units derived from propylene, (ii) isotactically arranged propylene derived sequences, and (iii) a heat of fusion less than 45 J/g.
2. The nonwoven fabric of paragraph 1, wherein the inner layers further comprise from 5 to 10 wt % of one or more hydrocarbon resins.
3. The nonwoven fabric of paragraphs 1 or 2, wherein the facing layers further comprise polypropylene or at least one thermoplastic resin.
4. The nonwoven fabric of any of paragraphs 1 to 3, wherein the facing layer has a permanent set above 50% and the inner layer has a permanent set below 27%.
5. The nonwoven fabric of any of paragraphs 1 to 4, wherein each facing layer is either spunbonded or meltblown.
6. The nonwoven fabric of any of paragraphs 1 to 5, wherein the one or more facing layers comprises at least one layer that is spunbonded and at least one layer that is meltblown.
7. The nonwoven fabric of any of paragraphs 1 to 6, wherein the one or more inner layers comprises at least one layer that is spunbonded and at least one layer that is meltblown.
8. The nonwoven fabric of any of paragraphs 1 to 7, wherein the one or more facing layers each comprise at least 80% by weight of the one or more propylene-based polymers.
9. A nonwoven fabric comprising:
   an inelastic nonwoven facing layer or layers comprising at least one polyolefin polymer, the inelastic layer having a permanent set above 30%;
   an elastic nonwoven layer or layers adjacent to the inelastic facing layer comprising a propylene-based polymer having 60 wt % or more units derived from propylene and isotactically arranged propylene derived sequences, the elastic layer having a permanent set below 28%.
10. The nonwoven fabric of paragraph 9, wherein the polyolefin polymer has a melt flow rate above 20 g/10 min.
11. The nonwoven fabric of paragraphs 9 or 10, wherein the polyolefin polymer is selected from the group consisting of polypropylene, copolymers of propylene and ethylene, polypropylene random copolymers, polypropylene impact copolymers, polyethylene, ethylene alpha olefin polymers and mixtures thereof.

12. The nonwoven fabric of any of paragraphs 9 to 11, wherein the inelastic nonwoven facing layer is fabricated using a spunbond or meltblown process.

13. The nonwoven fabric of any of paragraphs 9 to 12, wherein the propylene based polymer has a melt flow rate above 10 g/10 min.

14. The nonwoven fabric of any of paragraphs 9 to 13, wherein the propylene based polymer has a heat of fusion of less than 75 J/g.

15. The nonwoven fabric of any of paragraphs 9 to 14, wherein the propylene based polymer is modified with a slip additive.

16. The nonwoven fabric of any of paragraphs 9 to 15, wherein the propylene based polymer is modified with a hydrocarbon resin.

17. The nonwoven fabric of any of paragraphs 9 to 16, wherein the propylene based polymer is modified with a polyolefin having a melt flow rate greater than 400 g/10 min.

18. The nonwoven fabric of any of paragraphs 9 to 17, wherein the propylene based polymer is modified with one or more slip additives, hydrocarbon resins, or polyolefins having a melt flow rate greater than 400 g/10 min.

19. The nonwoven fabric of any of paragraphs 9 to 18, wherein the slip additive is selected from the group consisting of behenamide, erucamide, N-(2-hdriethyl) erucamide, Lauramide, N,N'-ethylene-bis-oleamide, N,N'-ethylene bissteamide, oleamide, oleyl palmitamide, stearyl erucamide, tallow amide, and mixtures thereof.

20. The nonwoven fabric of any of paragraphs 9 to 19, wherein the hydrocarbon resin is selected from the group consisting of aliphatic hydrocarbon resins, at least partially hydrogenated aliphatic hydrocarbon resins, aliphatic/aromatic hydrocarbon resins, at least partially hydrogenated aliphatic aromatic hydrocarbon resins, cycloaliphatic hydrocarbon resins, at least partially hydrogenated cycloaliphatic resins, aromatic hydrocarbon resins, at least partially hydrogenated aromatic hydrocarbon resins, at least partially hydrogenated aromatic hydrocarbon resins, polyterpene resins, terpene-phenol resins, rosins, rosin esters, hydrogenated rosins, hydrogenated rosin esters, and mixtures thereof.

21. The nonwoven fabric of any of paragraphs 17 to 20, wherein the polyolefin is selected from the group of polypropylene, propylene copolymers, polypropylene random copolymers, polypropylene impact copolymers, polyethylene, ethylene alpha olefin copolymers and mixtures thereof.

22. A nonwoven fabric, comprising:
one or more facing layers thermally bonded to one or more inner layers, wherein the facing layers are inelastic or partially elastic nonwoven webs comprising a blend of one or more propylene-based polymers and polypropylene, and wherein the inner layers are elastic nonwoven webs comprising one or more propylene-based polymers and one or more slip agents; and wherein the facing layers and inner layers have a difference in permanent set of at least 5%.

23. The nonwoven fabric of paragraph 22, wherein the inner layers further comprise one or more hydrocarbon resins.

24. The nonwoven fabric of paragraphs 22 or 23, wherein the one or more propylene-based polymers have (i) 60 wt % or more units derived from propylene, (ii) isotactically arranged propylene derived sequences, and (iii) a heat of fusion less than 45 J/g.

25. The nonwoven fabric of any of paragraphs 22 to 24, wherein each facing layer is either spunbonded or meltblown.

26. The nonwoven fabric of any of paragraphs 22 to 25, wherein the one or more facing layers comprise at least one layer that is spunbonded and at least one layer that is meltblown.

27. The nonwoven fabric of any of paragraphs 22 to 26, wherein the one or more inner layers comprise at least one layer that is spunbonded and at least one layer that is meltblown.

28. The nonwoven fabric of any of paragraphs 22 to 27, wherein the one or more facing layers each comprise at least 80% by weight of the one or more propylene-based polymers.

29. The nonwoven fabric of any of paragraphs 22 to 28, wherein the difference in permanent set is about 15% or more.

30. The nonwoven fabric of any of paragraphs 22 to 29, wherein the difference in permanent set is about 22% or more.

31. A disposable article comprising the nonwoven fabric of any of paragraphs 1 to 30.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention can be devised without departing from the basic scope thereof, and the scope thereof is determined by the claims that follow.

What is claimed is:
1. A nonwoven fabric, comprising:
(a) one or more facing layers that are each inelastic nonwoven webs having a permanent set above 30%, the one or more facing layers each comprising:
from about 5 to about 40 wt % polypropylene, and
from about 60 to about 95 wt % of a propylene-based polymer,
wherein the one or more facing layers are devoid of slip agents; and
(b) one or more inner layers that are elastic nonwoven webs having a permanent set below 28%, the one or more inner layers comprising:
one or more propylene-based polymers, and
from about 0.2 to about 10 wt. % of one or more slip agents,
wherein:
the propylene-based polymer has: (i) 60 wt % or more units derived from propylene, (ii) isotactically arranged propylene derived sequences, and (iii) a heat of fusion less than 45 J/g; and the one or more facing layers are thermally bonded to one or more inner layers; and the nonwoven fabric has an elongation greater than 150%.

2. The nonwoven fabric of claim 1, wherein the facing layer has a permanent set above 50% and the inner layer has a permanent set below 27%.

3. The nonwoven fabric of claim 1, wherein each facing layer is either spunbonded or meltblown.

4. The nonwoven fabric of claim 1, wherein the one or more facing layers comprises at least one layer that is spunbonded and at least one layer that is meltblown.

5. The nonwoven fabric of claim 1, wherein the one or more inner layers comprises at least one layer that is spunbonded and at least one layer that is meltblown.

6. The nonwoven fabric of claim 1, wherein the one or more facing layers each comprise from about 80% to about 95% by weight of the propylene-based polymer.

7. A nonwoven fabric comprising:
(a) an inelastic nonwoven facing layer or layers comprising:
from about 5 to about 40 wt % polypropylene and from about 60 to about 95 wt % of a propylene-based polymer,
wherein the inelastic layer has a permanent set above 30% and wherein the facing layers are devoid of slip agents; and
(b) an elastic nonwoven layer or layers thermally bonded to the inelastic facing layer comprising:
a slip additive,
a hydrocarbon resin,
a thermoplastic resin having a melt flow rate greater than 400 g/10 min, and
a propylene-based polymer
wherein the elastic layer has a permanent set below 28%; and
wherein the propylene-based polymer has 60 wt % or more units derived from propylene, isotactically arranged propylene derived sequences, and a heat of fusion less than 45 J/g; and
wherein the nonwoven fabric has an elongation greater than 150%.

8. The nonwoven fabric of claim 7, wherein the polypropylene has a melt flow rate above 20 g/10 min.

9. The nonwoven fabric of claim 7, wherein the inelastic nonwoven facing layer is fabricated using a spunbond or meltblown process.

10. The nonwoven fabric of claim 7, wherein the propylene-based polymer has a melt flow rate above 10 g/10 min.

11. The nonwoven fabric of claim 7, wherein the slip additive is selected from the group consisting of behenamide, erucamide, N-(2-hdriethyl) erucamide, Lauramide, N,N'-ethylene-bis-oleamide, N,N'-ethylene bisstearmide, oleamide, oleyl palmitamide, stearyl erucamide, tallow amide, and mixtures thereof.

12. The nonwoven fabric of claim 7, wherein the hydrocarbon resin is selected from the group consisting of aliphatic hydrocarbon resins, at least partially hydrogenated aliphatic hydrocarbon resins, aliphatic/aromatic hydrocarbon resins, at least partially hydrogenated aliphatic aromatic hydrocarbon resins, cycloaliphatic hydrocarbon resins, at least partially hydrogenated cycloaliphatic resins, aromatic hydrocarbon resins, at least partially hydrogenated aromatic hydrocarbon resins, at least partially hydrogenated aromatic hydrocarbon resins, polyterpene resins, terpene-phenol resins, rosins, rosin esters, hydrogenated rosins, hydrogenated rosin esters, and mixtures thereof.

13. The nonwoven fabric of claim 7, wherein the thermoplastic resin is selected from the group of polypropylene homopolymer, propylene copolymers, polypropylene random copolymers, polypropylene impact copolymers, polyethylene, ethylene alpha olefin copolymers and mixtures thereof.

14. A nonwoven fabric, comprising:
(a) one or more facing layers that are inelastic nonwoven webs comprising:
from about 5 to about 40 wt % polypropylene, and
from about 60 to about 95 wt % of a polypropylene-based polymer, and
(b) one or more inner layers that are elastic nonwoven webs comprising:
one or more propylene-based polymers and
one or more slip agents, and
wherein:
the facing layers are thermally bonded to inner layers;
the facing layers are devoid of slip agents;
the facing layers and inner layers have a difference in permanent set of at least 5%;
the propylene-based polymer has 60 wt % or more units derived from propylene, isotactically arranged propylene derived sequences, and a heat of fusion less than 45 J/g; and
the nonwoven fabric has an elongation greater than 150%.

15. The nonwoven fabric of claim 14, wherein each facing layer is either spunbonded or meltblown.

16. The nonwoven fabric of claim 14, wherein the one or more facing layers comprise at least one layer that is spunbonded and at least one layer that is meltblown.

17. The nonwoven fabric of claim 14, wherein the one or more inner layers comprise at least one layer that is spunbonded and at least one layer that is meltblown.

18. The nonwoven fabric of claim 14, wherein the one or more facing layers each comprise from about 80% to about 95% by weight of the propylene-based polymers.

19. The nonwoven fabric of claim 14, wherein the difference in permanent set is about 15% or more.

20. The nonwoven fabric of claim 14, wherein the difference in permanent set is about 22% or more.

21. A disposable article comprising the nonwoven fabric of claim 1.

22. A disposable article comprising the nonwoven fabric of claim 7.

23. A disposable article comprising the nonwoven fabric of claim 14.

24. The nonwoven fabric of claim 7, where the thermoplastic resin is polypropylene homopolymer.

25. The nonwoven fabric of claim 1, where the inner layers comprise propylene-based polymers and polypropylene.

26. The facing layer of claim 4, where the meltblown fabric includes a filament having a fiber diameter from 1 to 5 microns.

* * * * *